United States Patent
Stett et al.

(10) Patent No.: US 7,272,447 B2
(45) Date of Patent: Sep. 18, 2007

(54) ELECTRODE ARRANGEMENT FOR ELECTRICAL STIMULATION OF BIOLOGICAL MATERIAL, AND A MULTI-ELECTRODE ARRAY FOR USE IN SUCH AN ELECTRODE ARRANGEMENT

(75) Inventors: Alfred Stett, Reutlingen (DE); Wilfried Nisch, Tuebingen (DE); Martin Stelzle, Reutlingen (DE); Eberhart Zrenner, Tubingen (DE)

(73) Assignee: Retina Implant GmbH, Reutlingen (DE)

( * ) Notice: Subject to any disclaimer, the term of this patent is extended or adjusted under 35 U.S.C. 154(b) by 198 days.

(21) Appl. No.: 10/825,071

(22) Filed: Apr. 15, 2004

(65) Prior Publication Data

US 2004/0267344 A1 Dec. 30, 2004

Related U.S. Application Data

(63) Continuation of application No. PCT/EP02/10972, filed on Oct. 1, 2002.

(30) Foreign Application Priority Data

Oct. 17, 2001 (DE) ................. 101 51 650

(51) Int. Cl.
 *A61N 1/05* (2006.01)
 *A61N 1/36* (2006.01)
 *A61N 1/08* (2006.01)

(52) U.S. Cl. ................. 607/116; 607/53; 607/54; 607/141; 623/6.63; 623/4.1

(58) Field of Classification Search ............ 607/129, 607/52–54, 116, 6.63, 141; 623/6.63
See application file for complete search history.

(56) References Cited

U.S. PATENT DOCUMENTS

| 4,310,000 | A |  | 1/1982 | Lindemans |
|---|---|---|---|---|
| 4,628,933 | A |  | 12/1986 | Michelson |
| 5,016,633 | A |  | 5/1991 | Chow |
| 5,247,945 | A | * | 9/1993 | Heinze et al. ............ 607/129 |
| 5,674,264 | A |  | 10/1997 | Carter et al. |
| 5,944,747 | A |  | 8/1999 | Greenberg et al. |

(Continued)

FOREIGN PATENT DOCUMENTS

DE 195 25 570 A1 1/1996

(Continued)

OTHER PUBLICATIONS

Armin Bolz, *Die Bedeutung Der Phasengrenze Zwischen Alloplastischen Festkörpern und Biologischen Geweben Für Die Elektrostimulation*, Fachverlag Schiele & Schön p. 12-21,48-51 (1995).

(Continued)

*Primary Examiner*—Carl Layno
*Assistant Examiner*—Shevon Johnson
(74) *Attorney, Agent, or Firm*—Knobbe Martens Olson & Bear, LLP

(57) ABSTRACT

An electrode arrangement for electrical stimulation of biological material has at least one stimulation electrode via which the biological material can be fed a stimulus signal. Furthermore, a counter electrode is present which forms a counter pole to the stimulation electrode, one sensor electrode is provided with the aid of which it is possible to determine a polarization voltage across the stimulation electrode.

21 Claims, 2 Drawing Sheets

U.S. PATENT DOCUMENTS

| | | |
|---|---|---|
| 6,230,057 B1 | 5/2001 | Chow et al. |
| 6,269,268 B1 | 7/2001 | Callaghan et al. |
| 6,301,505 B1 | 10/2001 | Money |
| 6,390,971 B1 * | 5/2002 | Adams et al. ................ 600/25 |

FOREIGN PATENT DOCUMENTS

| | | |
|---|---|---|
| DE | 195 29 371 A1 | 2/1997 |
| DE | 197 05 988 A1 | 4/1998 |
| DE | 199 21 399 A1 | 11/2000 |

OTHER PUBLICATIONS

English translation of PCT International Preliminary Examination Report, Application No. PCT/EP2002/010972, European Patent Office (Feb. 2, 2004).

* cited by examiner

ELECTRODE ARRANGEMENT FOR ELECTRICAL STIMULATION OF BIOLOGICAL MATERIAL, AND A MULTI-ELECTRODE ARRAY FOR USE IN SUCH AN ELECTRODE ARRANGEMENT

CROSS-REFERENCES TO RELATED APPLICATIONS

This application is a continuation of copending international patent application PCT/EP02/10972 filed on Oct. 1, 2002 and designating the U.S., which was not published under PCT Article 21(2) in English, and claims priority of German patent application DE 101 51 650.9 filed on Oct. 17, 2001, which is incorporated herein by reference.

BACKGROUND OF THE INVENTION

1. Field of the Invention

The present invention relates to an electrode arrangement for electrical stimulation of biological material, having at least one stimulation electrode via which the biological material can be fed a stimulus signal, and having at least one counter electrode which forms a counter pole to the stimulation electrode.

The invention relates furthermore to a multi-electrode array for use in such an electrode arrangement.

2. Related Prior Art

An electrode arrangement of the said type and a corresponding multi-electrode array are disclosed, for example, in U.S. Pat. No. 4,628,933.

That document describes a so-called retina implant, that is to say an implant which is to be inserted in the region of the retina of an eye. The retina implant has a multiplicity of stimulation electrodes arranged in the manner of a field and with the aid of which artificially generated stimulus signals are fed to specific somatic cells located in the retina. The stimulus signals are generated with the aid of light-sensitive elements, of which the retina implant likewise has a multiplicity. The implant described is intended to restore at least a certain ability to see to people who have lost their ability to see, for example as a consequence of a disease known as retinitis pigmentosa.

After implantation, the stimulation electrodes of the described retina implant are in direct contact with the surrounding cell tissue and with body fluids which are present in the region of the cell tissue. It is known that so-called Helmholtz double layers form at the interface between the electrodes and the cell tissue or the body fluid, as happens generally at any phase transition between a metal electrode and an electrolytic liquid. The reason for this layer is the different type of charge transport in the said materials. The Helmholtz double layer constitutes in a first approximation an electric capacitor which is recharged upon stimulation of the cell tissue. This effect is denoted in the skilled community by the term electrode polarization, inter alia. A voltage which is denoted below as polarization voltage is then present across the charged electrode capacitor.

If the polarization voltage exceeds a certain threshold value, undesired redox reactions occur which can lead to irreversible tissue damage. Various methods are known in the prior art for the purpose of avoiding this.

It is proposed in the said U.S. Pat. No. 4,628,933 to arrange between the stimulation electrodes and the at least one counter electrode (denoted as ground conductor there) a large resistor via which the polarization voltage can be reduced. The coating of the electrodes with barium titanate or iridium is proposed as a further solution, since these materials are intended to have only a slight tendency to polarization. Moreover, the electric stimulation is intended to be performed with a rectangular alternating signal whose mean value is zero so that the interface capacitor is always discharged again.

In the German book entitled "Die Bedeutung der Phasengrenze zwischen alloplastischen Festkörpern und biologischen Geweben für die Elektrostimulation" ["The importance of the interface between alloplastic solids and biological tissues for electrostimulation"] by Armin Bolz, published by Fachverlag Schiele und Schön, 1994, it is proposed, with reference to the said problem, for the stimulation electrode and the counter electrode to be cyclically short-circuited with the aid of a so-called autoshort switch, in order to achieve a quick charge reduction at the interface (loc. cit. page 49).

A further approach to avoiding undesired reactions consists in dimensioning the capacitance of the phase transition, by the configuration of the electrode surfaces, to be as large as possible in order to minimize the polarization voltage. Moreover, parameters of the stimulus signal such as, in particular, the pulse durations and pulse amplitudes, can be dimensioned so as to exclude undesired reactions even under worst-case conditions. Finally, it is possible in principle to calculate the polarization voltage from the pulse durations and pulse amplitudes of the stimulus signal in order to control the stimulation on the basis of the results.

None of the known methods is optimum, however. Precisely the last-mentioned measures have the disadvantage that transient processes are above all detected, whereas no account is taken of a static electrode polarization rising in the course of time. Consequently, it is necessary in practice to take account of safety reserves in the dimensioning, and this renders optimum stimulation of the cell tissue difficult.

The regular or continuous discharge of the interface capacitor impairs the degrees of freedom in the temporal dimensioning of the stimulus signals. Likewise, the use of zero-point symmetrical alternating signals constrains the freedom of configuration. In addition, some of the measures are certainly well suited for excluding undesired reactions in the region of one or a few electrodes. However, if a multiplicity of electrodes, that is to say a multi-electrode array, is used for the stimulation of the cell tissue such as, for example, in the case of a retina implant, real time monitoring for the avoidance of undesired reactions is very complicated.

SUMMARY OF THE INVENTION

In view of the above, it is an object of the present invention to specify an electrode arrangement of the type mentioned at the outset which on the one hand provides many degrees of freedom in the configuration of the stimulus signals and, on the other hand, permits reliable suppression of undesired reactions.

This and other objects are achieved with an electrode arrangement of the type mentioned at the outset, in which, furthermore, at least one sensor electrode is present with the aid of which it is possible to determine a polarization voltage across the stimulation electrode.

The electrode arrangement according to the invention is particularly advantageous in conjunction with a multi-electrode array in which a multiplicity of stimulation electrodes and a multiplicity of sensor electrodes are arranged on a common substrate.

By contrast with the multiplicity of previous approaches, the solution proposed here is based on the idea of detecting the actual polarization across the stimulation electrode as exactly as possible and in real time, in order to permit optimum control of the stimulus signal as a function of the real measurement results obtained. This approach for the first time permits a far-reaching freedom of configuration in dimensioning the stimulus signal without increasing the risk of undesired reactions in an uncontrolled fashion in the region of the stimulation electrodes. Whereas all previous approaches have intentionally or unintentionally avoided creating further interfaces, which after all are the fundamental cause of the undesired reactions, through additional electrodes, the present invention adopts precisely this approach. Specifically, it has surprisingly been shown that the new possibilities of configuration compensate very well the disadvantages previously to be expected.

It has been shown, in particular, that the risks to be expected inherently as a consequence of the additional interface surfaces are substantially reduced when the flow of current via the interface is reduced or even largely suppressed. Precisely this is a very good possibility with the sensor electrode according to the invention, since the determination of the polarization voltage can also be implemented without an appreciable flow of current. Surprisingly, it is therefore possible to use the sensor electrode according to the invention without increasing the risk of undesired redox reactions.

Moreover, it was not to be expected to date that the polarization voltage across the stimulation electrode can at all be determined with the aid of an additional sensor electrode which makes tissue contact.

Particularly in conjunction with multi-electrode arrays, the solution according to the invention has the advantage that it is possible for undesired redox reactions to be avoided in real time such that damage to the cell tissue can be excluded in a particularly reliable way. Moreover, it is also possible in this case for static components of the electrode polarization to be reliably detected, and this further increases the safety.

A further advantage consists in that the stimulus signal can be adapted to slow variations in the contact situation in the case of chronic implants. A variation in the contact situation arises, for example, when fibrotic tissue forms in the region of the electrodes as a consequence of the stimulation.

Further, the sensor electrode according to the invention also for the first time permits exact control of the stimulus signal independently of the avoidance of undesired reactions, specifically in real time and as a function of the real ambient conditions. The stimulation of the tissue can therefore be carried out in a very targeted and finely dosed fashion.

According to one object of the invention, the electrode arrangement further includes a difference element with at least two inputs, a first input being connected to the stimulation electrode, and a second input being connected to the sensor electrode.

The difference element is preferably a difference amplifier employed in known circuit engineering. The high-resistance input of such difference amplifiers very greatly reduces the flow of current in the determination of the polarization voltage, and so an additional polarization voltage, falsifying the measuring signal, across the sensor electrode is avoided, and consequently the advantages already previously mentioned come to bear particularly strongly. Moreover, the measure has the advantage that the difference element provides the relevant polarization voltage across the stimulation electrode directly and without further computational steps. As a result of this, it is possible to monitor the electrode polarization in real time in a simple and effective way.

According to a further object, the electrode arrangement further includes an interrupter which interrupts the stimulus signal as a function of the determined polarization voltage.

This measure virtually implements an emergency stop switch with the aid of which a stimulus signal applied from outside can be interrupted immediately when the electrode polarization reaches critical values. Undesired redox reactions can thereby be suppressed even more reliably.

According to a further object of the previously mentioned measure, the interrupter is a changeover switch which short-circuits the stimulation electrode and the counter electrode.

The electrode polarization can be reduced particularly quickly by this measure when a critical threshold value is reached, thus increasing the reliability of the arrangement once more.

According to a further object, the electrode arrangement further includes a control loop which varies at least one parameter of the stimulus signal as a function of the determined polarization voltage.

This measure aims less at the abrupt disconnection of a stimulus signal for the purpose of avoiding undesired redox reactions, than at an optimum setting of the stimulus signal. In particular, parameters such as pulse durations or pulse amplitudes, and even the dynamic range of the stimulus signal itself can be set very exactly. The measure has the advantage that the actual stimulation of the cell tissue can be carried out in an optimum operating range, the avoidance of undesired redox reactions being ensured simultaneously. The abrupt disconnection of a stimulus signal can thereby largely be avoided.

In a further embodiment, the electrode arrangement further includes a memory in which a maximum value of the polarization voltage can be stored. This memory can preferably be written to and/or read from in a wireless fashion.

The measure has the advantage that a maximum permissible highest value of the polarization voltage can be stored in a simple way such that the electrode arrangement can easily be adapted to individual requirements of a patient. The stored maximum value can be used, in particular, as a reference threshold upon the exceeding of which the previously mentioned interrupter undertakes an emergency shut down of the stimulus signal. Alternatively, or in addition, the memory can also be written to during operation of the electrode arrangement with the respectively highest measured value of the polarization voltage. This measure permits a later control and documentation of a stimulation that has been carried out. The wireless connection of the memory is particularly preferred when the electrode arrangement is implanted permanently in the human body, for example in the case of a retina implant. It is easily possible in this case to access the memory from outside.

In a further embodiment, the sensor electrode is arranged in the immediate vicinity of the stimulation electrode.

This measure enables a particularly exact determination of the critical polarization of the stimulation electrode. Consequently, the stimulus signal can be led in an optimum range with a very narrow tolerance.

In a further embodiment, the sensor electrode is arranged next to the stimulation electrode.

This measure is very simple as regards production technology and therefore enables a cost-effective implementation of the arrangement according to the invention.

In a further embodiment, the sensor electrode is arranged concentrically with the stimulation electrode.

This measure is particularly advantageous for detecting the polarization of the stimulation electrode as exactly as possible with the aid of the sensor electrode without making compromises with regard to the effectively active area of the stimulation electrode. As already indicated further above, a large interface capacitor has the advantage of minimizing the electrode polarization. A large interface capacitor may be achieved, in turn, by the largest possible area of the stimulation electrode. The concentric arrangement enables an optimum combination of the requirements for a large area of the stimulation electrode and a specially more compact, but not restrictive arrangement of the sensor electrode.

In a further embodiment, the sensor electrode at least partially surrounds the stimulation electrode.

It is particularly preferred when the sensor electrode is arranged as a thin ring around the stimulation electrode. This measure is a particularly efficient possibility of optimizing the electrode arrangement with regard to the previously mentioned parameters.

In an alternative embodiment, the sensor electrode is arranged in a cutout in the stimulation electrode.

This measure is also very well suited with regard to an optimum arrangement of the sensor electrode together with optimization of the stimulation electrode.

In a further embodiment, the sensor electrode and the stimulation electrode are planar structures.

The measure is particularly advantageous with regard to multi-electrode arrays, since planar structures enable cost-effective production of a multiplicity of electrodes. The previously mentioned advantageous refinements, in particular, can be implemented in an especially simple and cost-effective fashion.

According to a further object, the sensor electrode is small by comparison with the stimulation electrode.

In this case the size specification relates chiefly to the active area of the sensor electrode or of the stimulation electrode. The smaller the sensor electrode, the more space there is available for configuring the stimulation electrode, as a result of which it is possible to implement the advantageously large capacitor already mentioned. Moreover, the stimulation of the cell tissue is not disadvantageously influenced in the case of a small sensor electrode.

In a further embodiment, the sensor electrode and the stimulation electrode are produced from the same material.

This measure is particularly advantageous with regard to the production costs, since the two electrodes can hereby be produced in a common production step. Moreover, electrochemical voltages between the two electrodes are avoided, something which could otherwise disadvantageously influence both the measuring signals and the stimulus signals.

In a further embodiment, a multiplicity of stimulation electrodes and a multiplicity of sensor electrodes are arranged on a common substrate.

This measure likewise enables a particularly cost-effective and rational fabrication of the arrangement according to the invention.

In a further embodiment of the abovementioned measure, at least one sensor electrode is arranged in the region of each stimulation electrode.

This measure enables a particularly exact control of the stimulus signals. The measure is particularly advantageous in the case of multi-electrode arrays and, moreover, in combination with the above-described geometrical electrode shapes.

It goes without saying that the above-named measures and those still to be explained below can be used not only in the combination respectively specified, but also in other combinations or on their own without departing from the scope of the present invention.

BRIEF DESCRIPTION OF THE DRAWINGS

Embodiments of the invention are illustrated in the drawing and explained in more detail in the following description. In the drawing.

DESCRIPTION OF PREFERRED EMBODIMENTS

Figure 1:
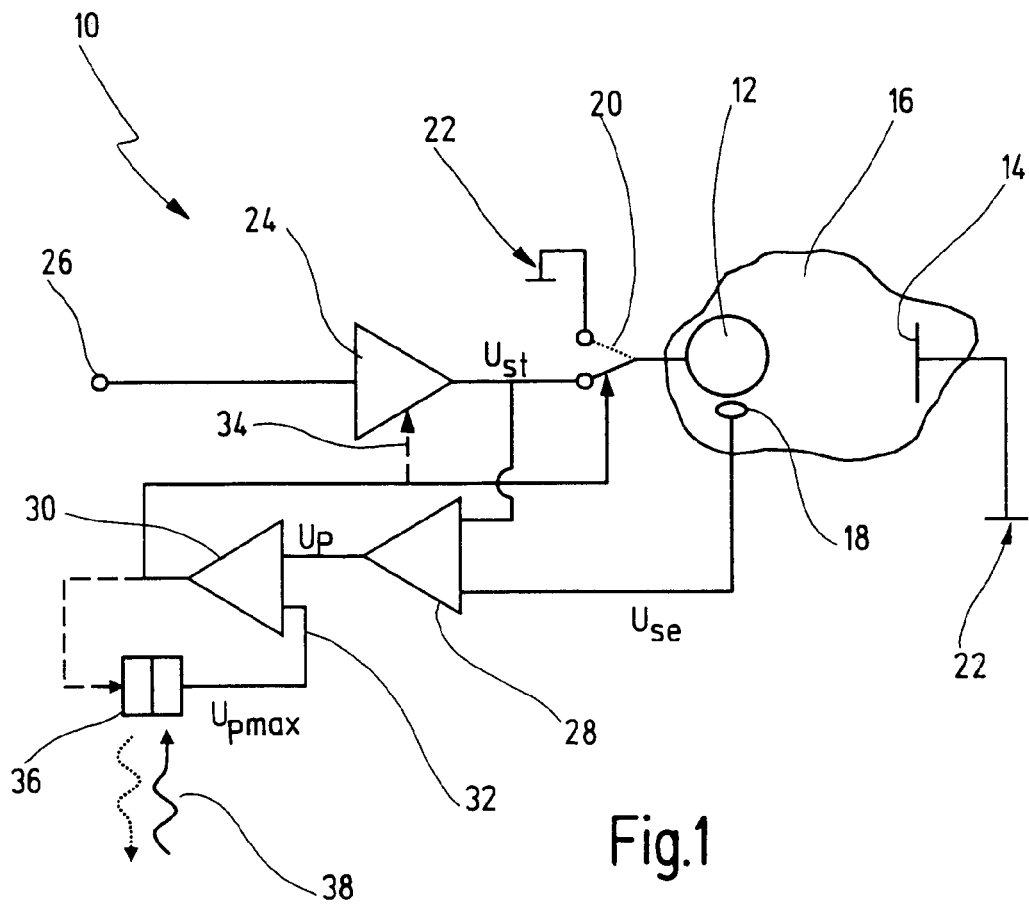
FIG. 1 shows a sketch of the circuit of a preferred electrode arrangement according to the invention.

An electrode arrangement according to the invention is denoted in FIG. 1 in its entirety by the reference numeral 10.

The electrode arrangement 10 includes a stimulation electrode 12 which is produced using planar technology. However, the invention is not restricted thereto. In other exemplary embodiments, the stimulation electrode and the sensor electrode are arranged in a "3-D arrangement", that is to say in mutually offset planes. The reference numeral 14 denotes a counter electrode which forms the counter pole (ground) for the stimulation electrode 12. The two electrodes 12, 14 serve the purpose of electrically stimulating biological material, in the present example a cell tissue 16, in a way known per se.

In a preferred embodiment of the invention, the cell tissue 16 is a tissue in the region of the retina of the human eye. The stimulation electrode 12 and the further subsequently described constituents of the electrode arrangement 10 are implanted in this case in the patient's eye either epiretinally or, preferably, subretinally.

In another preferred embodiment, the cell tissue 16 is a tissue in the region of the brain or the peripheral nervous system.

In accordance with the present invention, the reference numeral 18 denotes a sensor electrode which is arranged in the immediate vicinity, although independently, of the stimulation electrode. The area of the sensor electrode 18 is small by comparison with the area of the stimulation electrode 12.

The reference numeral 20 denotes a changeover switch which optionally connects the stimulation electrode 12 to one of two alternative potentials. The reference numeral 22 denotes a ground potential which is identical to the permanent potential of the counter electrode. The changeover switch 20 connects the stimulation electrode 12 to the ground potential 22 when a critical polarization of the stimulation electrode has been detected with the aid of the sensor electrode 18. The critical polarization of the stimulation electrode 12 can be very quickly reduced in this way in order to avoid undesired redox reactions in the region of the cell tissue 16.

In the alternative second switch position, the changeover switch 20 connects the stimulation electrode 12 to the output of a signal amplifier 24 to whose input 26 a stimulus signal can be applied. This switch position of the changeover switch 20 is the normal case in the proper operation of the electrode arrangement 10.

In accordance with the preferred embodiment in which the electrode arrangement 10 is a constituent of a retina implant, the stimulus signal is generated with the aid of light-sensitive elements (multi-photodiode array, not illustrated here). The basic design of such a retina implant is known, for example, from DE 199 21 399 A1, DE 197 05 988 A1 or from DE 195 29 371 A1, to which reference is made in full here as regards further details of the retina implant.

The reference numeral 28 denotes a difference amplifier at whose first input the voltage $U_{se}$ picked up by the sensor electrode 18 is present. Present at the second input is the output signal of the signal amplifier 24, which corresponds to the operating voltage $U_{st}$ of the stimulation electrode 12 in normal working operation of the electrode arrangement 10. The difference amplifier 28 forms the difference between the two voltages $U_{st}$ and $U_{se}$, which corresponds to the relevant polarization voltage $U_p$ ($U_p = U_{st} - U_{se}$). The output signal of the difference amplifier 28, that is to say the specific polarization voltage $U_p$, is fed to a first input of a comparator 30. Present at the second input 32 thereof is a reference voltage which constitutes the maximum permissible polarization voltage $U_{pmax}$ in the illustrated preferred embodiment. The output signal of the comparator 30 determines the switch position of the changeover switch 20. Moreover, in a preferred embodiment of the invention it also determines the gain of the signal amplifier 24, the dynamic range thereof or another suitable parameter. This dependence is illustrated by a signal tap 34 in FIG. 1. The result of this is a control loop for the optimum setting of the stimulus signal.

Otherwise than in the embodiment shown in FIG. 1, the signal tap 34 can also be taken off directly at the output of the difference amplifier 28. In this case, the control signal for the signal amplifier 24 is directly proportional to the polarization voltage determined, that is to say it is then not "digitized" via the comparator.

The reference numeral 36 denotes a memory which here can be written to and read from from the outside in a wireless fashion. This is indicated by the arrows 38. The maximum permissible highest value of the polarization voltage $U_{pmax}$ is stored here in the memory 36. Furthermore, the respectively measured highest value of the polarization voltage $U_p$ or, as shown in FIG. 1, the output signal of the comparator 30 can be stored in the memory 36 in order to enable a later monitoring and documentation of the stimulation.

The electrode arrangement 10 permits various controls or regulations of the stimulus signal. For example, it is possible to stimulate the cell tissue 16 with the aid of current pulses, the voltage present across the stimulation electrode 12 rising in accordance with the known charging curve of a capacitor. With the aid of the sensor electrode 18 and the difference amplifier 28, it is possible to switch off the current pulse when the polarization of the stimulation electrode 12 exceeds the maximum permissible value $U_{pmax}$. In this case, the electrode arrangement 10 includes, as it were, a safety circuit.

In another application, the electrode arrangement 10 serves rather as an adaptation circuit for setting an optimum stimulus signal. By determining the respectively current polarization voltage $U_p$ with the aid of the sensor electrode 18, the maximum permissible parameters (amplitude, pulse duration, etc.) of the stimulus signal can be determined and set. In some applications, the output signal of the difference amplifier 28 is also led to the outside in this case via a tap (not illustrated separately here), in order to be available there as measured value for external regulating and measuring circuits.

In the case of the preferred application of the electrode arrangement 10 in a retina implant, the output signal of the difference amplifier 28 is advantageously also used for the purpose of setting the operating point, and thus the photosensitivity of the light-sensitive elements. In the case of a retina implant in accordance with DE 199 21 399 A1 already mentioned, the operating point of the reference elements described there can advantageously also be set in this way.

The electrode arrangement 10 is preferably implemented using CMOS technology, something which is possible very simply and cost-effectively on the basis of the analogue components used.

Figure 2:
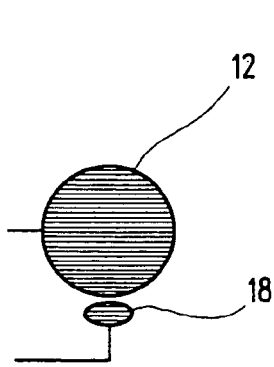
FIGS. 2 to 4 show preferred exemplary embodiments of stimulation and sensor electrodes.
Figure 3:
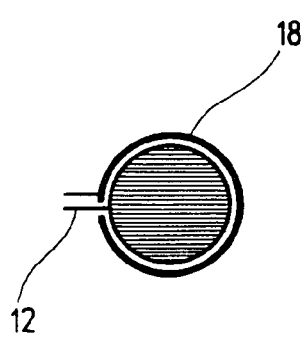
Figure 4:
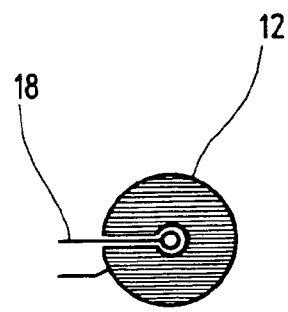

Preferred embodiments of stimulation electrodes 12 and sensor electrodes 18 are illustrated in FIGS. 2 to 4. The reference numerals used correspond in this case to those from FIG. 1. The sensor electrode 18 in FIG. 2 is a patch which is small by comparison with the stimulation electrode 12 and is arranged next to the stimulation electrode 12. In FIG. 3, the sensor electrode 18 surrounds the stimulation electrode 12 concentrically in the form of a thin annulus. In FIG. 4, the stimulation electrode 18 is arranged centrally in a cutout in the centre of the stimulation electrode 12. In this case, the stimulation electrode 12 surrounds the sensor electrode 18 concentrically.

The stimulation electrode 12 is illustrated as a circle in all three cases. Such a design has proved to be advantageous in practice. However, other geometries, for example square electrode surfaces, are also possible in addition. The sensor electrode 18 in this case has an appropriately adapted geometry.

Figure 5:
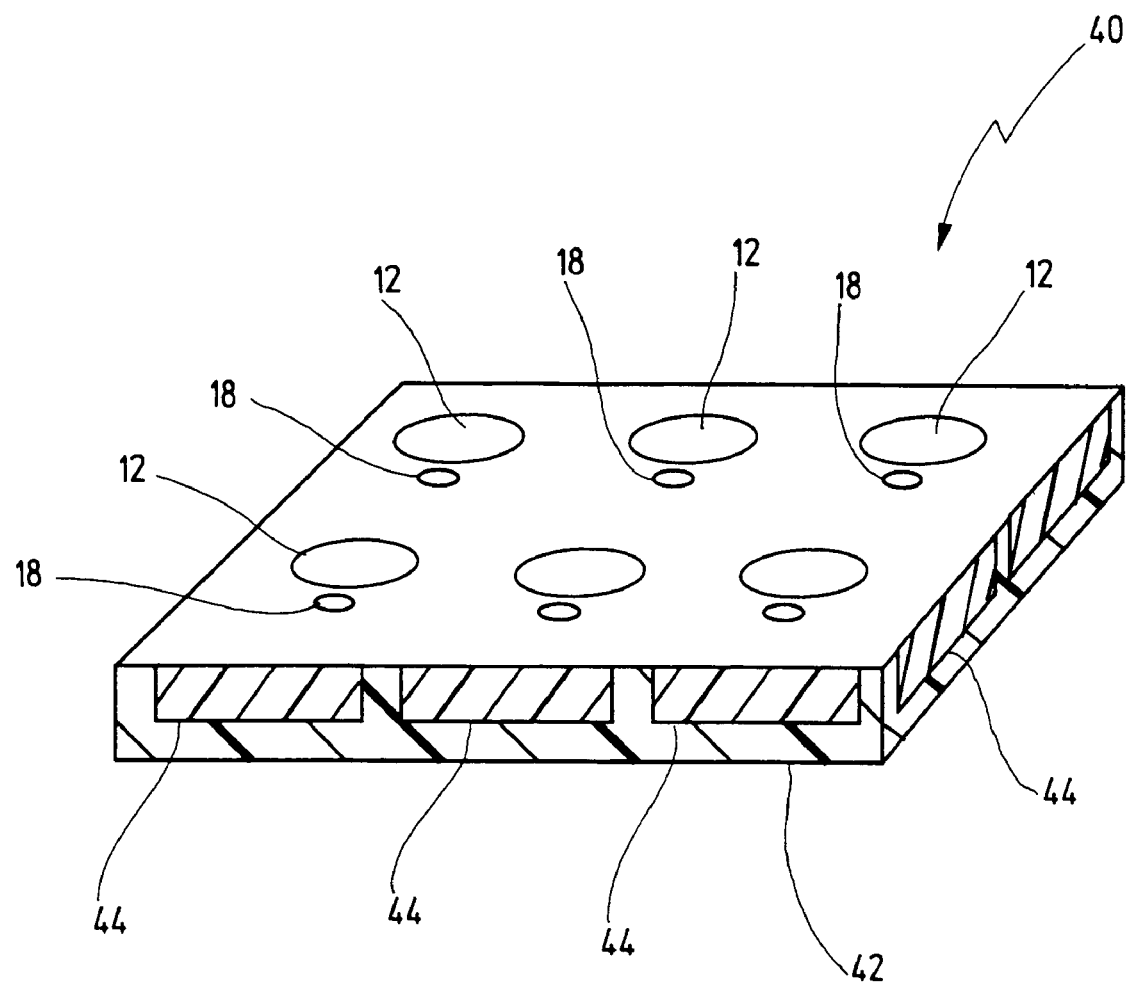
FIG. 5 shows a simplified illustration of a multi-electrode array using planar CMOS technology, with the inventive electrode arrangement from FIG. 1.

A multi-electrode array according to the invention is denoted in its entirety by the reference numeral 40 in FIG. 5. The multi-electrode array, which is a component of a retina implant in a preferred embodiment, includes a substrate 42 on which a multiplicity of stimulation electrodes 12 and sensor electrodes 18 are arranged. Moreover, there are embedded in the substrate 42 in a way known per se CMOS structures 44 with the aid of which the changeover switch 20, the signal amplifier 24, the difference amplifier 28, the comparator 30 and further circuit components not illustrated here in more detail are implemented. In the case of a retina implant, the substrate 42 (chip) also further includes the light-sensitive elements and the further required control electronics.

Although the above description of embodiments was given chiefly with regard to the preferred application in a retina implant, the inventive electrode arrangement can also be used advantageously in any other application for the purpose of stimulating biological material. In particular, an advantageous use is possible in micro-electrode arrays which are employed in vitro for the purposes of simulation or for diagnostic purposes. The advantages of the inventive electrode arrangement come to bear more in this case the higher the number, and thus the packing density, of the stimulation electrodes.

Therefore, what is claimed, is:

1. An electrode arrangement for electrical stimulation of biological material, comprising:
   at least one stimulation electrode via which the biological material can be fed a stimulus signal;
   at least one counter electrode which forms a counter pole to the stimulation electrode;
   at least one sensor electrode configured to determine a polarization voltage across the stimulation electrode, wherein the sensor electrode is distinct from the stimulation and counter electrodes; and
a control loop configured to vary at least one parameter of the stimulus signal as a function of the determined polarization voltage.

2. An electrode arrangement for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, which electrode arrangement further includes a memory in which a maximum value of the polarization voltage can be stored, wherein the memory can be written to and/or read from in a wireless fashion.

3. An electrode arrangement for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, wherein the sensor electrode is arranged concentrically with the stimulation electrode.

4. An electrode arrangement for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, wherein the sensor electrode at least partially surrounds the stimulation electrode.

5. An electrode arrangement for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, wherein the sensor electrode is arranged in a cutout in the stimulation electrode.

6. An electrode arrangement for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, wherein the sensor electrode and the stimulation electrode are planar structures.

7. An electrode arrangement for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, wherein the sensor electrode is small by comparison with the stimulation electrode.

8. An electrode arrangement for electrical stimulation of biological material comprising;
at least one stimulation electrode via which the biological material can be fed a stimulus signal;
at least one counter electrode which forms a counter pole to the stimulation electrode;
at least one sensor electrode configured to determine a polarization voltage across the stimulation electrode, wherein the sensor electrode and the stimulation electrode are produced from the same materials, and wherein the sensor electrode is distinct from the stimulation and counter electrodes.

9. An electrode arrangement for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, wherein a multiplicity of stimulation electrodes and a multiplicity of sensor electrodes are arranged on a common substrate.

10. The electrode arrangement of claim 9, wherein at least one sensor electrode is arranged in the region of each stimulation electrode.

11. A retina implant for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode.

12. The retina implant of claim 11, wherein a multiplicity of stimulation electrodes and a multiplicity of sensor electrodes are arranged on a common substrate.

13. The retina implant of claim 12, which further includes a difference element with at least two inputs, a first input being connected to the stimulation electrode, and a second input being connected to the sensor electrode.

14. A retina implant for electrical stimulation of biological material, having at least one stimulation electrode via which the biological material can be fed a stimulus signal, and having at least one counter electrode which forms a counter pole to the stimulation electrode, wherein at least one sensor electrode is provided with the aid of which it is possible to determine a polarization voltage across the stimulation electrode, and wherein a multiplicity of stimulation electrodes and a multiplicity of sensor electrodes are arranged on a common substrate.

15. The retina implant of claim 14, which further includes an interrupter which interrupts the stimulus signal as a function of the determined polarization voltage.

16. The retina implant of claim 15, wherein the interrupter is a changeover switch which short-circuits the stimulation electrode and the counter electrode.

17. The retina implant of claim 14, wherein the sensor electrode is arranged in the immediate vicinity of the stimulation electrode.

18. The retina implant of claim 14, wherein the sensor electrode is arranged next to the stimulation electrode.

19. The retina implant of claim 14, which further includes a difference element with at least two inputs, a first input being connected to the stimulation electrode, and a second input being connected to the sensor electrode.

20. The retina implant of claim 19, which further includes an interrupter which interrupts the stimulus signal as a function of the determined polarization voltage.

21. The retina implant of claim 20, wherein the interrupter is a changeover switch which short-circuits the stimulation electrode and the counter electrode.

* * * * *

UNITED STATES PATENT AND TRADEMARK OFFICE
CERTIFICATE OF CORRECTION

PATENT NO. : 7,272,447 B2 Page 1 of 1
APPLICATION NO. : 10/825071
DATED : September 18, 2007
INVENTOR(S) : Stett et al.

It is certified that error appears in the above-identified patent and that said Letters Patent is hereby corrected as shown below:

Title Page, item 56, column 2, line 3, please delete "12-21,48-51" and insert -- 12-21, 48-51 --, therefor.

Column 7, line 24, please delete "Upmaxin" and insert -- Upmax in --, therefor.

Column 7, line 41 (approx.), before "the outside" please delete "from".

Column 9, line 63, in Claim 8, after "comprising" please delete ";" and insert -- : --, therefor.

Column 10, line 4, in Claim 8, please delete "materials," and insert -- material, --, therefor.

Signed and Sealed this

Twentieth Day of May, 2008

JON W. DUDAS
*Director of the United States Patent and Trademark Office*